US010508094B2

(12) United States Patent
Powell et al.

(10) Patent No.: US 10,508,094 B2
(45) Date of Patent: Dec. 17, 2019

(54) METHODS FOR PRODUCING FERRIC MALTOL COMPOSITIONS FROM FERROUS HYDROXIDES

(71) Applicant: Shield TX (UK) Limited, Gateshead (GB)

(72) Inventors: Jonathan Joseph Powell, Cambridge (GB); Nuno Jorge Rodrigues Faria, Milton Ernest (GB)

(73) Assignee: SHIELD TX (UK) LIMITED, Gateshead, Tyne and Wear (GB)

( * ) Notice: Subject to any disclaimer, the term of this patent is extended or adjusted under 35 U.S.C. 154(b) by 0 days.

(21) Appl. No.: 16/089,801

(22) PCT Filed: Mar. 31, 2017

(86) PCT No.: PCT/EP2017/057703
§ 371 (c)(1),
(2) Date: Sep. 28, 2018

(87) PCT Pub. No.: WO2017/167970
PCT Pub. Date: Oct. 5, 2017

(65) Prior Publication Data
US 2019/0127344 A1 May 2, 2019

(30) Foreign Application Priority Data

Mar. 31, 2016 (GB) .................. 1605501.4

(51) Int. Cl.
*C07D 309/40* (2006.01)
(52) U.S. Cl.
CPC ................. *C07D 309/40* (2013.01)

(58) Field of Classification Search
CPC .................................................... C07D 309/40
See application file for complete search history.

(56) References Cited

U.S. PATENT DOCUMENTS

2005/0250754 A1* 11/2005 Stockham ............ C07D 309/40
514/184

FOREIGN PATENT DOCUMENTS

| WO | WO 03/097627 | 11/2003 |
|----|----|----|
| WO | WO 2008/096130 | 2/2008 |
| WO | WO 2012/101442 | 8/2012 |
| WO | WO 2015/101971 | 1/2015 |

OTHER PUBLICATIONS

Gasche et al. "Ferric maltol is effective in correcting iron deficiency anemia in patients with inflammatory bowel disease: results from a phase-3 clinical trial program." *Inflammatory Bowel Diseases* 21.3 (2014): 579-588.
Harvey et al. "Ferric trimaltol corrects iron deficiency anaemia in patients intolerant of iron." *Alimentary Pharmacology & Therapeutics* 12.9 (1998): 845-848.
International Search Report and Written Opinion issued in International Application No. PCT/EP2017/057703, dated May 19, 2017.
Search Report issued in United Kingdom Application No. GB1605501.4, dated Jan. 19, 2017.

* cited by examiner

*Primary Examiner* — Timothy R Rozof
(74) *Attorney, Agent, or Firm* — Parker Highlander PLLC

(57) ABSTRACT

Methods for producing ferric maltol compositions, such as ferric trimaltol, from ferrous hydroxides, are described, as well as ferric maltol compositions produced by these methods and their uses.

25 Claims, 1 Drawing Sheet ically appropriate grades are
still required if the ferric trimaltol is to be suitable for human
administration and hence are comparatively expensive starting
materials. Importantly, the use of non-carboxylate iron
salts (e.g. ferric chloride) results in the addition of considerable
levels of the respective counter-anion (e.g. three
moles of chloride per every mole of iron) of which a
significant part is retained in the filtration (or centrifugation)
cake and thus must be washed off. As such, WO 2012/
101442 does not address the problem of product losses in
WO 03/097627. Furthermore, the addition of a non-carboxylate
iron salt (e.g. ferric chloride) to a very alkaline solution,
as described in WO 2012/101442, promotes the formation of
stable iron oxides, which is an unwanted contaminant in
ferric trimaltol. As a consequence, further costly and time-consuming
processing of the material would be required for
manufacturing.

Overall, the cost of the current aqueous syntheses is
driven by regulatory demands for low levels of toxic heavy
metals and residual reagents in the final pharmaceutical
formulation, which force the use of highly purified, and thus
expensive, iron salts as well as thorough washing of the final
product (resulting in significant losses of product). This will
impact on the final price of ferric trimaltol and potentially
limits patient access to this therapy. As such, there is a need
for a process that can use lower iron grades and limited wash
cycles, whilst producing ferric trimaltol of adequate purity.

Accordingly, it remains a problem in the art to provide
processes for the synthesis of ferric trimaltol at economic
cost and which overcome some or all of the drawbacks set
out above that are associated with prior art. Solving these
issues through better synthesis of the material would allow
good patient access to ferric trimaltol.

SUMMARY OF THE INVENTION

Broadly, the present invention relates to methods for
producing ferric maltol compositions, such as ferric trimaltol,
in which maltol is reacted with a ferrous hydroxide.
Ferrous hydroxide, despite containing Fe at +2 valence and
in a form that is generally considered of low reactivity
compared to ferrous salts, was found to be a good source of
iron in the synthesis of ferric maltol. This is even more
surprising given that iron hydroxides are generally regarded
as an unwanted by-product in ferric maltol syntheses. However,
in the methods of the present invention it is shown that
ferrous hydroxide is capable of gradually oxidising, and
subsequently releasing ferric iron ions that are capable of
being complexed by maltol.

Accordingly, in a first aspect, the present invention provides
a method for producing a ferric maltol composition
comprising reacting ferrous hydroxide with maltol and
recovering the ferric maltol that forms. In a preferred
embodiment, the present invention provides a method for
producing a ferric trimaltol composition comprising reacting
ferrous hydroxide with maltol and recovering the ferric
trimaltol that forms.

Usefully, the dissolution of ferrous hydroxide results in
the release of hydroxyl ions which can be used to dissolve
maltol. As such, the inventors also observed that maltol can
be used as a slurry or suspension, rather than as a solution
as disclosed in previous processes, and consequently lower
amounts of sodium or potassium contamination (from

METHODS FOR PRODUCING FERRIC MALTOL COMPOSITIONS FROM FERROUS HYDROXIDES

This application is a national phase application under 35
U.S.C. § 371 of International Application No. PCT/EP2017/
057703, filed Mar. 31, 2017, which claims priority to United
Kingdom Application No. 1605501.4, filed Mar. 31, 2016.
The entire text of each of the above referenced disclosures
is specifically incorporated herein by reference.

FIELD OF THE INVENTION

The present invention relates to methods for producing
ferric maltol compositions, such as ferric trimaltol, from
ferrous hydroxides, and to ferric maltol compositions produced
by these methods and their uses.

BACKGROUND OF THE INVENTION

The sugar derivative maltol is a hydroxypyrone (IUPAC
name: 3-hydroxy-2-methyl-4H-pyran-4-one) and it strongly
chelates iron and the resulting complex (ferric trimaltol
which may also be written as ferric tri-maltol) is well
absorbed, unlike many other ferric iron therapies. Ferric
trimaltol appears well tolerated even in populations highly
susceptible to gastrointestinal side-effects, such as IBD
patients (Harvey et al., 1998), and as such it provides a
valuable alternative to patients who are intolerant of oral
ferrous iron products, notably in place of intravenous iron.
Clinical trials using ferric trimaltol have been carried out,
see for example, Gasche et al., 2015.

However, despite the evidence of bioavailability and
tolerability for ferric trimaltol, its clinical development has
been limited by the absence of adequate synthetic routes. In
particular, most manufacturing processes require the use of
organic solvents, which increase manufacturing costs, for
example to deal with post-synthesis solvent removal, and
require additional safety measures, for example to deal with
flammability. Critically, solvent-based syntheses are not
robust and often generate ferric hydroxide, described in the
prior art to be an unwanted impurity of the synthesis.

WO 03/097627 (Vitra Pharmaceuticals Limited)
describes the synthesis of ferric trimaltol from iron salts of
carboxylic acids in aqueous solution at a pH greater than 7.
In a first synthesis, ferric citrate is added to a solution of
sodium hydroxide at room temperature and maltol is added
to a second solution of sodium hydroxide at pH 11.6. The
ferric citrate solution is added to the maltol solution, leading
to the production of a deep red precipitate. This composition
is then evaporated until dryness and the material is powdered
and dried. Alternative syntheses are described using
ferrous fumarate or ferrous gluconate as the iron carboxylate
salt starting material, and by dissolving maltol in sodium
carbonate solution in place of sodium hydroxide. However,
despite the fact that this process is fully aqueous, several of
the iron carboxylate salts employed are expensive, especially
as they need to be pharmaceutical grade if the ferric
trimaltol is to be suitable for human administration. More
importantly, this process introduces high levels of carboxylates
(equimolar to iron or greater) to the synthesis that are
not easily removed by filtration or centrifugation of the
ferric trimaltol cake. Instead these water soluble contaminants
must be washed off (e.g. water washed), but this would
result in considerable losses of the product due to the
amphipathic nature of ferric trimaltol.

WO 2012/101442 (Iron Therapeutic Holdings AG)
describes the synthesis of ferric trimaltol by reacting maltol
and a non-carboxylate iron salt in an aqueous solution at
alkaline pH. However, despite the lower cost of non-carboxylate iron salts, pharmaceut sodium or potassium hydroxide used to dissolve maltol) are likely to be present in the final product compared to previously disclosed syntheses. This cycle of the release of hydroxyl ions causing maltol to dissolve has the advantage that the pH of the reaction does not substantially increase as the ferrous hydroxide dissolves and so results in comparatively low levels of sodium or potassium contamination in the final product as less sodium or potassium hydroxide is needed to dissolve the maltol slurry.

By way of illustration, at the start of the synthesis, the pH will preferably be above 8.0, more preferably above 8.5 and most preferably above 9.0. Generally the pH will be below 12.0, more preferably below 11.6 and most preferably below 11.0. The pH can be adjusted with by addition of a base, preferably sodium hydroxide or sodium carbonate.

Importantly, unlike previous syntheses that use ferric salts and thus add unwanted reactants (e.g. chloride, citrate), ferrous hydroxide slurries can be cleaned up after synthesis, for example, by filtering and re-suspending in water (or other appropriate solvents), and therefore do not contribute to unwanted contaminants in the final ferric maltol product. As noted above, the present inventors also observed that complexation of iron (from ferrous hydroxide) by maltol releases hydroxyl ions that help to further dissolve maltol, and as such this ferrous hydroxide method does reduces the possibility of unwanted counter anions in the final product.

Alternatively or additionally, given that ferrous hydroxides are predominantly formed at pHs greater than 6, it is possible to add an optional pre-neutralisation step up to, for example, pH 5 causing hydrolytic metals such as aluminium or chromium to precipitate and allowing their removal (e.g. filtration) before the production of the ferrous hydroxide gel. This advantageous feature allows the use of lower grades of iron, if so intended.

Additionally or alternatively, the methods of the present invention that are described herein may provide the further advantage of enabling syntheses from ferrous hydroxides produced from elemental iron (zero valence), thereby enabling ferric trimaltol to be produced from a very inexpensive source of iron, e.g. as compared to the more expensive iron salts used as starting materials in WO 03/097627 and WO 2012/101442. A still further advantage is that the methods for producing ferric trimaltol according to the present invention may enable single vessel synthesis, for example using a single manufacturing vessel, such as a filtration unit with overhead stirring.

Taken together, the method of the present invention enable unwanted solutes to be removed from ferrous hydroxide intermediates. This is highly advantageous as it enables the production of high purity ferric maltol compositions in a straightforward manner from a cheaper source of iron to that required in the prior art.

In contrast, without the formation of ferrous hydroxides intermediates, used in the methods of the present invention, single vessel syntheses based on forming soluble non-carboxylate iron salts (e.g. ferric chloride) from elemental iron are not commercially practical, since the large concentration of unwanted salts formed or added during the synthesis (e.g. chloride from hydrochloric acid) contaminate the product and are not easily removed. For example, a large excess of hydrochloric acid would be needed for this dissolution process to occur within an acceptable time-frame for a manufacturing processes and/or crystallisation of ferric chloride to remove excess of chloride is not facile. In addition, a single vessel synthesis in which soluble iron carboxylate salts (e.g. ferric citrate) are formed for subsequent conversion to ferric trimaltol would not be industrially feasible since dissolution of elemental iron by carboxylates is orders of magnitude slower than with strong mineral acids and the clean-up of unwanted solutes would not be practical. In the present invention, unreacted iron may be easily removed with a magnet.

In some aspects, the maltol used in the methods of the present invention is provided as a slurry or a suspension. In this situation, the reaction between the ferrous hydroxide releases hydroxyl ions as the ferric iron ions (upon oxidation from ferrous) are complexed by maltol, leading to the dissolution of further maltol in the slurry. This cycle of the release of hydroxyl ions causing maltol to dissolve has the advantage that the pH of the reaction does not substantially increase as the ferrous hydroxide dissolves, and so results in comparatively low levels of sodium or potassium contamination in the final product as less sodium or potassium hydroxide is needed to dissolve the maltol slurry.

Generally, the ferrous hydroxide is produced from a ferrous iron solution at 0.2M, or 0.5 M, or 1 M Fe or greater, and may be produced from a ferrous iron solution by raising the pH.

Generally, the ferrous hydroxide is added to a maltol solution at a concentration of 0.6M, 1.5M, 3M or greater. By way of illustration, the ferrous hydroxide is added to a maltol solution to provide a maltol to iron ratio in solution equal to or greater than 3 and lower than 3.75. More preferably greater than 3.1 and lower than 3.5. Preferably, the ferrous hydroxide is added to a maltol solution which is at a pH greater than 8.5, preferably greater than 9.0.

By ferrous hydroxide we mean a material that contains some ferrous hydroxide, which may be coated or doped with other molecules such as ligands, but the preferred embodiment is a pure or suitably pure ferrous hydroxide because this minimises the clean up stages required for the final product (i.e. the recovery of a suitably pure ferric maltol). Ferrous hydroxide can be determined by analytical techniques known in the art such as spectroscopic, microscopic, electrophoretic and techniques that identify iron's redox status.

In a further aspect, the present invention provides a method for preparing a ferric maltol composition which comprises the steps of:
  (a) preparing a ferrous iron solution from a ferrous iron salt (e.g. ferrous chloride);
  (b) precipitating ferrous hydroxide slurry by raising pH; also optionally under an oxygen free or reduced oxygen atmosphere;
  (c) after step (a) or (b), optionally ligand doping or ligand coating the ferrous hydroxide;
  (d) optionally removing and discarding a soluble fraction containing unused reactants or unwanted solutes, such as chloride or sodium or potassium;
  (e) optionally washing the retained pellet with water;
  (f) re-suspending the pellet in water, or other appropriate solvents or solvent mixtures, and optionally adjusting pH;
  (g) reacting the ferrous hydroxide slurry with an alkaline solution or slurry of maltol to produce ferric maltol optionally in the presence of a reaction promoting material;
  (h) recovering and optionally washing the ferric maltol; and
  (i) optionally drying the ferric maltol.

In a further aspect, the present invention provides a method for producing an iron supplement comprising ferric maltol, the process comprising having produced ferric maltol composition according to a method as described herein, the further step of formulating the ferric maltol for administration to a subject.

Embodiments of the present invention will now be described by way of example and not limitation with reference to the accompanying figures. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIGS. 1 and 2: UV vis conditions: Perkin Elmer Lambda 25; 700-350 nm; 480 nm/min; 0.5 nm interval.

DETAILED DESCRIPTION

Ferric Maltols

Figure 1:
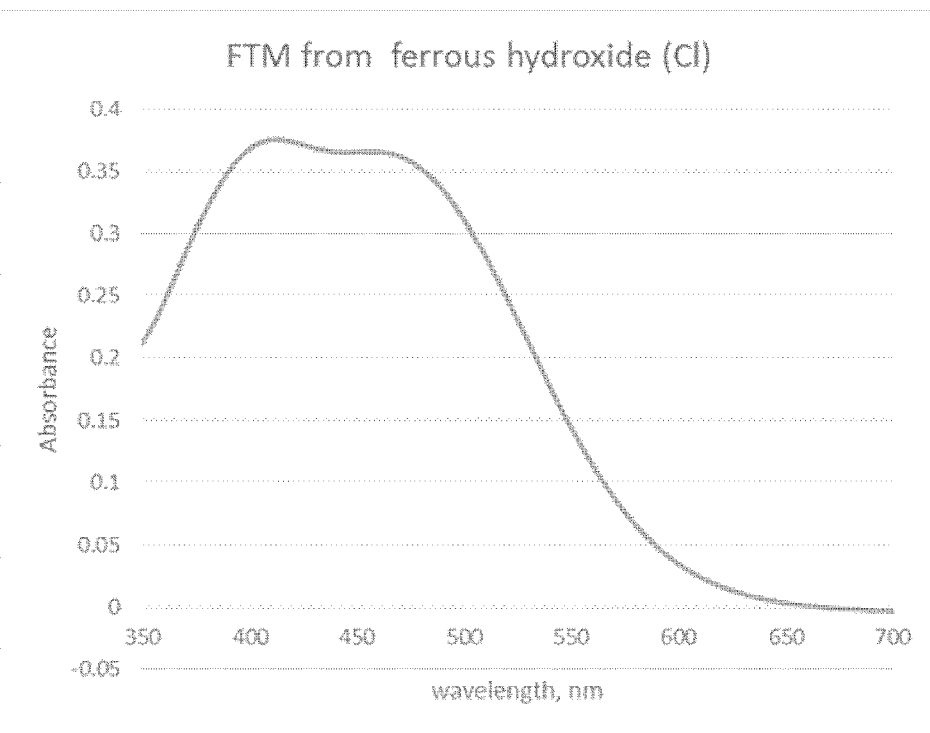
FIG. 1. UV-vis spectra of ferric trimaltol produced from ferrous hydroxide which had been produced from ferrous chloride (as per Example 1). The two band profile is characteristic of ferric trimaltol recovered from an alkaline environment.
Figure 2:
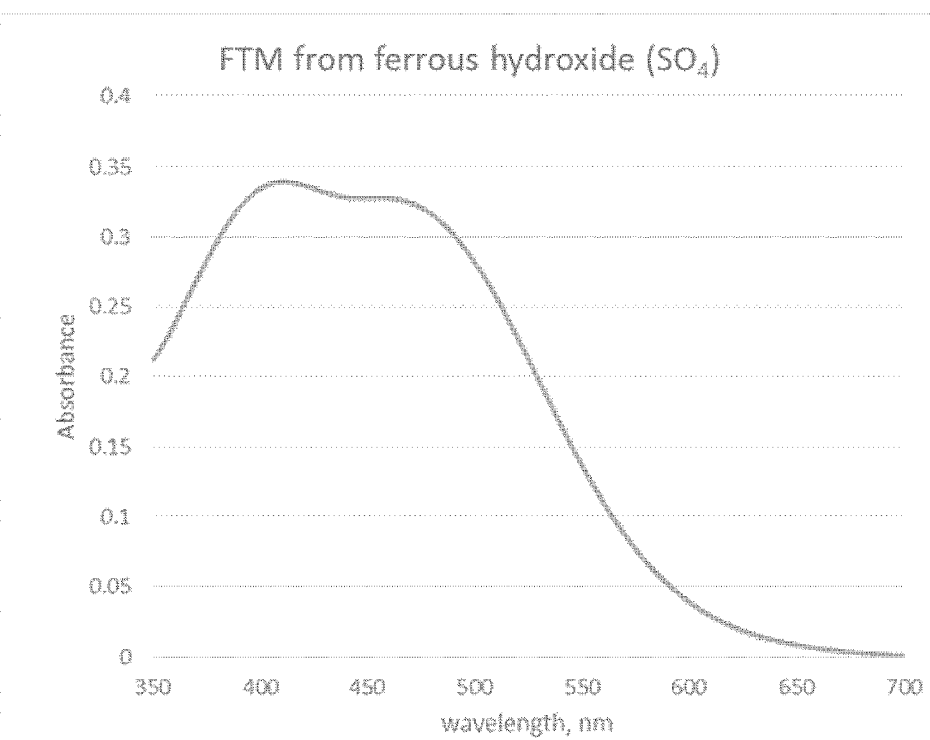
FIG. 2. UV-vis spectra of ferric trimaltol produced from ferrous hydroxide which had been produced from ferrous sulphate (as per example 2). The two band profile is characteristic of ferric trimaltol recovered from an alkaline environment.

Ferric maltols are a class of compounds that include ferric trimaltol, a chemical complex formed between ferric iron ($Fe^{3+}$) and the hydroxypyrone, maltol (IUPAC name: 3-Hydroxy-2-methyl-4H-pyran-4-one), in a molar ratio of ferric iron to maltol of 3:1. Maltol strongly chelates the ferric iron and the resulting complex (ferric trimaltol) is well absorbed, in contrast to some other ferric iron supplements, fortificants and therapies. Maltol binds metal cations mainly in the form of a dioxobidentate ligand in a similar manner proposed for other 4(1H)-pyranones:

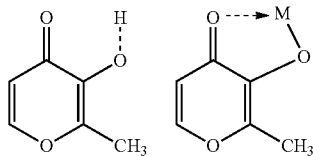

Structure of maltol (3-hydroxy-2-methyl-4(H)-pyran-4-one) and dioxo-chelation to metal cations (M) such as iron. For ferric trimaltol three maltol groups surround one iron.

However, particularly in aqueous environments, it is well known that concentration-dependent and pH-dependent equilibrium species of ferric maltol can form that include oligomeric species such as dimers and/or ferric iron species complexed with one or two maltol molecules. Ferric trimaltol in solid or powder form may also exist as oligomers including dimers and not every iron is necessarily co-ordinated to three maltol molecules, but the term ferric tri-maltol is conventionally used in the art. Accordingly, in the present application, references to "ferric maltol" are intended to include ferric iron species complexed with one, two or three maltol species, as well as oligomeric species such dimers and other species that may exist in equilibrium with them, and to mixtures of any of these species, even though the behaviour of the complex is believed to be dominated by its trimaltol form at supplemental levels.

The structure of ferric trimaltol is shown in WO 2015/101971 (Iron Therapeutics Holdings AG). Ferric trimaltol is also known as "ST10" and is generally administered as a 30 mg dose, where 30 mg refers to the amount iron in the dose. The amount of ST10 equivalent to 30 mg of elemental iron ($Fe^3$) is 231.5 mg. Ferric trimaltol has undergone clinical trials for the treatment or prevention of anaemia in particular in patients with inflammatory bowel disease (IBD) or in patients with intolerance of oral iron.

Ferrous Hydroxides

The ferrous hydroxides described herein can be produced in a similar manner to other iron hydroxides, typically by adding a base to a ferrous iron salt solution or dissolving elemental iron with a strong mineral acid (e.g., hydrochloric acid), optionally followed by base addition. Preferably, this reaction is carried out under an oxygen free or reduced oxygen atmosphere, as the presence of at least some oxygen in the reaction will mean that some of the iron will precipitate as ferric hydroxide, rather than ferrous hydroxide. However, it is generally preferred that at least 50% or more of the iron in the iron hydroxide is ferrous iron, more preferably at least 60%, more preferably at least 70%, more preferably at least 80%, and most preferably at least 90% of the iron.

However, ferrous iron ions are less hydrolytic than ferric iron ions and thus precipitation of ferrous hydroxides occurs at higher pHs, typically pH 5 or greater (depending on the concentration of ferrous iron). As per the teachings of the present invention, the oxidation of ferrous iron in the ferrous hydroxides should be limited prior to addition to the maltol solution or suspension or slurry. As such, synthesis may be carried out under an inert atmosphere (e.g., nitrogen). In contrast, ferrous to ferric iron oxidation is a desired feature upon addition of the ferrous hydroxides to the maltol solution (or slurry) and indeed can be accelerated, if so intended, by introducing air or oxygen to the reaction vessel.

In some embodiments, the ferrous iron compositions may be ligand modified or ligand coated as described in our earlier application WO 2008/096130, which is expressly incorporated by reference in its entirety. These approaches may also be employed to make the ligand modified ferrous hydroxides used as one of the starting materials for making ferric maltol compositions in the methods of the present invention.

Ligand-coated materials are widely known in the art. These are distinct from ligand-modified materials, in that ligands are used to coat the particle surface rather than disrupt their mineral core. In the synthetic processes described herein, ferrous hydroxides are coated with organic ligands, which increases the materials' dispersibility and/or reduces their drive towards aggregation.

WO 2008/096130 sets out that ligand modified metal oxo-hydroxides constitute forms of matter that differ from both conventional stoichiometric metal coordination complexes and from particles of metal hydroxide that have been physically coated with ligand molecules. Ligand modified metal hydroxides can be defined, inter alia, with reference to structural, spectroscopic or compositional parameters (i.e., using the analytical signatures of the materials) or by the processes by which the materials have been obtained. Thus, while metal hydroxide powders are very well known in the field of inorganic chemistry, when they are modified by suitable ligands (i.e. other than oxo or hydroxy groups) this may alter their physical and/or chemical properties to produce new materials and for use in new applications.

Ligand modified ferrous hydroxides are formed when a ferrous iron salt is dissolved and then induced to precipitate by an increase in pH leading to the formation of polymeric ferrous hydroxide in the presence of one or more ligand species. This process results in some of the ligand species becoming incorporated into the solid phase structure of the ferrous hydroxide.

A range of ligands may be used in the production of the ligand modified or ligand coated ferric hydroxides used in the synthesis of ferric maltols, such as ferric trimaltol, in the methods of the present invention, and the ligand modified ferric hydroxides may comprise one, two, three, four or more different species of ligands. Typically, ligands are incorporated in the ligand modified ferrous hydroxides to aid in the modification of a physico-chemical property of the material, e.g. as compared to unmodified or uncoated ferric hydroxides, in particular to aid in reaction that allows for the synthesis of ferric trimaltol. Examples of ligands that may be employed in the present invention include, but are by no means limited to: carboxylic acids such as adipic acid, glutaric acid, tartaric acid, malic acid, succinic acid, aspartic acid, pimelic acid, citric acid, gluconic acid, lactic acid or benzoic acid; food additives such as maltol, ethyl maltol or vanillin; amino acids such as lysine, tryptophan, glutamine, proline, valine, or histidine; and/or ionised forms thereof. Typically ligands may be well recognised in the art as having high affinity for a certain metal ion in solution or as having only low affinity or not be typically recognised as a ligand for a given metal ion at all. Typically, one ligand or two ligands of differing affinities for the metal ion are used in the production of these materials although zero, one, two, three, four, five or more different species of ligands may be useful in certain embodiments of the methods of the present invention.

The ligand may be a carboxylic acid ligand, or an ionised form thereof (i.e., a carboxylate ligand), such as tartaric acid or tartrate. A more preferred group of carboxylic acid ligands include tartaric acid or tartrate, adipic acid (or adipate), glutaric acid (or glutarate), pimelic acid (or pimelate), succinic acid (or succinate), and malic acid (or malate). A further preferred type of ligand are amino acids such as lysine, tryptophan, glutamine, proline, valine, or histidine. Preferably, a low cost amino acid such as lysine is used in the synthesis. Whether the ligand is present as the acid or is partially or completely ionised and present in the form of an anion will depend on a range of factors such as the pH at which the material is produced and/or recovered, the use of post-production treatment or formulation steps and how the ligand becomes incorporated into the oxo-hydroxy metal ion material. In some embodiments with carboxylic acids, at least a proportion of the ligand will be present in the carboxylate form as the ferric hydroxide materials are typically recovered at pH>4 and because the interaction between the ligand and the positively charged iron would be greatly enhanced by the presence of the negatively charged carboxylate ion. For the avoidance of doubt, the use of carboxylic acid ligands in accordance with the present invention covers all of these possibilities, i.e. the ligand present as a carboxylic acid, in a non-ionised form, in a partially ionised form (e.g., if the ligand is a dicarboxylic acid) or completely ionised as a carboxylate ion, and mixtures thereof. Similarly, the use of the word amino acid covers all its possible ionisation forms. The molar ratio of the ferric ion(s) to the ligand(s) (L) is also a parameter of the solid phase ligand-modified poly oxo-hydroxy metal ion materials that can be varied according to the methods disclosed herein to vary the properties of the materials. Generally, the useful ratios of M:L will be between 10:1, 5:1, 4:1, 3:1, 2:1 and 1:1.

Ferric Maltol Compositions and their Uses

The ferric maltol compositions produced according to the methods of the present invention may be formulated for administration to an individual and contain in addition to ferric trimaltol, a pharmaceutically acceptable excipient, carrier, buffer, stabiliser or other materials well known to those skilled in the art. Such materials should be non-toxic and should not interfere with the efficacy of the solid phase materials for the application in question.

As described herein, ferric maltols, such as ferric trimaltol, have particular uses in the treatment of iron deficiency. By way of example, the ferric trimaltol compositions may be used to deliver iron to an individual for use in the prophylaxis or treatment of iron deficiency or iron deficiency anaemia which may be suspected, or diagnosed through standard haematological and clinical chemistry techniques. Iron deficiency and iron deficiency anaemia may occur in isolation, for example due to inadequate nutrition or due to excessive iron losses, or they may be associated with stresses such as pregnancy or lactation, or they may be associated with diseases such as inflammatory disorders, cancers and renal insufficiency. In addition, there is evidence that the reduced erythropoiesis associated with anaemia of chronic disease may be improved or corrected by the effective delivery of systemic iron and that co-delivery of iron with erythropoietin or its analogues may be especially effective in overcoming reduced erthropoietic activity. Thus, by way of further example, the ferric trimaltol compositions disclosed herein may be used to deliver iron to an individual for use in the treatment of sub-optimal erythropoietic activity such as in anaemia of chronic disease. Anaemia of chronic disease may be associated with conditions such as renal insufficiency, cancer and inflammatory disorders. As noted above, iron deficiency may also commonly occur in these disorders so it follows that treatment through iron supplementation may address iron deficiency alone and/or anaemia of chronic disease. It will be recognised by those skilled in the art that the above examples of the medical uses of iron supplements are by no means limiting.

In addition, ferric trimaltol is currently used for the treatment or prevention of anaemia in particular in patients with inflammatory bowel disease (IBD) or in patients with intolerance to other forms of oral iron.

The precise nature of the carrier or other component may be related to the manner or route of administration of the composition. These compositions may be delivered by a range of delivery routes including, but not limited to: gastrointestinal delivery, including orally and per rectum or by implantation at specific sites, including prosthetics that may be used for this purpose or mainly for another purpose but have this benefit.

Pharmaceutical compositions made according to the present invention are generally for oral administration and may be in a tablet, capsule, powder, gel or liquid form. A tablet may include a solid carrier such as gelatin or other excipients. Capsules may have specialised properties such as an enteric coating. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The ferric trimaltol compositions used in accordance with the present invention that are to be given to an individual are preferably administered in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

In general, ferric trimaltol may be used as a form of oral iron supplementation for nutritional or medical benefit. In this area, there are three main examples:

(i) Therapeutic (prescription) supplements, which are generally administered by the oral or i.v. routes for the treatment of indications including iron deficiency anaemia, iron deficiency and anaemia of chronic disease. The therapeutic administration of materials of the present invention may be in conjunction with other therapies and especially with the concomitant use of erythropoietin.

(ii) Nutritional (self prescribed/purchased supplements) which are usually for oral delivery.

(iii) Fortificants. These may be traditional forms—in terms of being added to food prior to purchase—or more recent fortificant forms such as 'Sprinkles' which are added (rather like salt or pepper) to food at the time of ingestion.

In all formats, but most especially for fortificants, subsequent formulation, such as addition of a protective coating (e.g. lipid), may be necessary to make the material compatible with its intended usage.

It will be recognised by those skilled in the art that the above examples of the medical uses of iron supplements are by no means limiting.

EXAMPLES

Example 1: Ferric Trimaltol from Ferrous Hydroxide (Produced from Ferrous Chloride)

Synthesis of Ferrous Hydroxide Gel 10.93 g $FeCl_2 \cdot 4H_2O$ was added to 50 mL UHP water, which had been bubbled with $N_2$ for 5 min. Whilst still bubbling $N_2$, 19.7 mL NaOH 5M was added, producing a ferrous hydroxide gel. Unwanted soluble species were then removed by centrifuging the gel and disposing of the supernatant. The ferrous hydroxide gel was then resuspended in water back to its original volume prior to being added to the maltol slurry.

Ferric Trimaltol Synthesis 3.0 g NaOH pellets was added to 30 mL UHP water and stirred until dissolved. Next, 24.5 g maltol was added and stirred. This produced a slurry in which most of the maltol remained undissolved. Next, the ferrous hydroxide gel was gradually added to this solution with vigorous stirring during which the remainder of maltol dissolved. Following overnight incubation in a non-sealed vessel (to allow ingress of oxygen), a red dark precipitate (i.e., ferric trimaltol) was formed. Finally, the material was recovered by centrifugation and dried overnight (55° C.).

Example 2: Ferric Trimaltol from Ferrous Hydroxide (Produced from Ferrous Sulphate)

Synthesis of Ferrous Hydroxide Gel 15.29 g $FeSO_4 \cdot 7H_2O$ was added to 100 mL UHP water, which had been bubbled with $N_2$ for 5 min. Then 1.5 mL of $H_2SO_4$ (95-98% w/w) was added to assist with the dissolution of ferrous sulphate. Next, whilst still bubbling $N_2$, 34.5 mL NaOH 5M was added, thus raising the pH to 9.45 and resulting in the formation of the ferrous hydroxide gel. Unwanted soluble species were then removed by centrifuging the gel and disposing of the supernatant. The ferrous hydroxide gel was then resuspended in water back to 100 mL prior to being added to the maltol slurry.

Ferric Trimaltol Synthesis 2.75 g NaOH pellets was added to 30 mL UHP water and stirred until dissolved. Next, 24.5 g maltol was added and stirred. This produced a slurry in which most of the maltol remained undissolved. Next, the ferrous hydroxide gel was gradually added to this solution with vigorous stirring during which the remainder of maltol dissolved. Following overnight incubation in a non-sealed vessel (to allow ingress of oxygen), a red dark precipitate (i.e. FTM) was formed (final pH 11.05). The FTM material was then washed three times by centrifuging, disposing of supernatant and re-suspending back in water. Finally, the material was recovered by centrifugation and dried overnight (45° C.).

Previously disclosed synthetic processes for the production of ferric trimaltol under aqueous conditions require the addition of NaOH (or other suitable bases) for conversion maltol from its protonated form to its deprotonated form prior to complexation of iron. However this results in the formation of unwanted sodium ions which must be washed off. In contrast, the use of ferrous hydroxides according to the methods of the present invention reduces the requirements for base and associated counter cation (e.g. sodium), which is a favourable feature.

REFERENCES

All publications, patent and patent applications cited herein or filed with this application, including references filed as part of an Information Disclosure Statement are incorporated by reference in their entirety.

Gasche et al., Ferric maltol is effective in correcting iron deficiency anaemia in patients with inflammatory bowel disease: results from a phase-3 clinical trial program. *Inflamm Bowel Dis.*, 21(3):579-88, 2015.

Harvey et al., Ferric trimaltol corrects iron deficiency anaemia in patients intolerant of iron. *Aliment Pharmacol Ther.*, 12(9):845-8, 1998.

The invention claimed is:

1. A method for producing a ferric maltol composition comprising reacting ferrous hydroxide with maltol and recovering the ferric maltol that forms.

2. The method according to claim 1, wherein the ferric maltol is ferric trimaltol.

3. The method according to claim 1, wherein the ferrous hydroxide is ligand modified ferrous hydroxide or ligand coated ferrous hydroxide.

4. The method according to claim 1, wherein the ferrous hydroxide is in the form of a colloid or gel.

5. The method according to any claim 1, further comprising producing the ferrous hydroxide.

6. The method according to claim 5, wherein the reducing environment is an oxygen depleted environment.

7. The method according to claim 1, wherein the maltol is in the form of a slurry or suspension of maltol.

8. The method according to claim 1, wherein the reaction of the ferrous hydroxide oxidises to produce ferric hydroxide that is then complexed by maltol to form ferric maltol.

9. The method according to claim 8, wherein the complexation of the ferric hydroxide releases hydroxyl ions, leading to further dissolution of maltol in the slurry or suspension.

10. The method according to claim 1, wherein the method comprises a pre-neutralisation step for removing hydrolytic metal ions, such as ferric iron ($Fe^{3+}$), aluminium ($Al^{3+}$) and chromium ($Cr^{3+}$) prior to producing the ferrous hydroxide.

11. The method according to claim 10, wherein the pre-neutralisation step comprises adjusting the pH of the reaction be below the pH at which less than 10% of the ferrous ions convert to ferrous hydroxide and above the pH at which the hydrolytic metal ions precipitate.

12. The method according to claim 1, wherein the method is carried out under fully aqueous conditions.

13. The method according to claim 1, further comprising the initial step of producing the ferrous hydroxide.

14. The method according to claim 13, wherein the ferrous hydroxide is obtained from ferrous chloride or ferrous sulphate.

15. The method according to claim 13, comprising producing the ferrous hydroxide from elemental iron, and optionally removing unreacted iron with a magnet.

16. The method according to claim 15, wherein the elemental iron is dissolved in a strong mineral acid, such as hydrochloric acid.

17. The method according to claim 1, wherein the ferric maltol is produced in a single vessel.

18. The method according to claim 1, further comprising separating, and optionally drying the ferric maltol composition.

19. The method according to claim 1, further comprising purifying and/or formulating the ferric maltol composition.

20. The method according to claim 1, further comprising mixing the ferric maltol composition with one or more excipients.

21. The method according to claim 1, comprising the steps of:
(a) preparing a ferrous iron solution from a ferrous iron salt;
(b) precipitating ferrous hydroxide slurry by raising pH; also optionally under an oxygen free or reduced oxygen atmosphere;
(c) after step (a) or (b), optionally ligand doping or ligand coating the ferrous hydroxide;
(d) optionally removing and discarding a soluble fraction containing unused reactants or unwanted solutes, such as chloride or sodium or potassium;
(e) optionally washing the retained pellet with water;
(f) re-suspending the pellet in water, or other appropriate solvents or solvent mixtures, and optionally adjusting pH;
(g) reacting the ferrous hydroxide slurry with an alkaline solution or slurry of maltol to produce ferric maltol optionally in the presence of a reaction promoting material;
(h) recovering and optionally washing the ferric maltol; and
(i) optionally drying the ferric maltol.

22. The method according to claim 21, wherein the ferric maltol is ferric trimaltol.

23. The method according to claim 1, further comprising formulating the ferric maltol composition for oral administration to a subject.

24. The method according to claim 5, wherein the reaction is carried out in a reducing environment.

25. The method according to claim 21, wherein the ferrous iron salt is ferrous chloride.

* * * * *